(12) United States Patent
Mehrmohammadi et al.

(10) Patent No.: US 10,952,700 B2
(45) Date of Patent: Mar. 23, 2021

(54) ULTRASOUND AND PHOTOACOUSTIC SYSTEMS AND METHODS FOR FETAL BRAIN ASSESSMENT DURING DELIVERY

(71) Applicant: Wayne State University, Detroit, MI (US)

(72) Inventors: Mohammad Mehrmohammadi, Farmington Hills, MI (US); Edgar Hernandez-Andrade, Grosse Pointe Farms, MI (US); Juri G. Gelovani, Detroit, MI (US); Sonia S. Hassan, Novi, MI (US); Yan Yan, Detroit, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 186 days.

(21) Appl. No.: 15/880,902

(22) Filed: Jan. 26, 2018

(65) Prior Publication Data
US 2018/0214119 A1 Aug. 2, 2018

Related U.S. Application Data

(60) Provisional application No. 62/451,392, filed on Jan. 27, 2017.

(51) Int. Cl.
*A61B 5/1455* (2006.01)
*A61B 8/08* (2006.01)
(Continued)

(52) U.S. Cl.
CPC .......... *A61B 8/0866* (2013.01); *A61B 5/0095* (2013.01); *A61B 5/14552* (2013.01);
(Continued)

(58) Field of Classification Search
None
See application file for complete search history.

(56) References Cited

U.S. PATENT DOCUMENTS

| 6,498,942 B1 | 12/2002 | Esenaliev et al. |
| 6,751,490 B2 | 6/2004 | Esenaliev et al. |
| (Continued) | | |

FOREIGN PATENT DOCUMENTS

| WO | WO2013188709 A1 | 12/2013 |
| WO | WO2016007678 A1 | 1/2016 |

OTHER PUBLICATIONS

Yan-Yan, "Compact Endovaginal Ultrasond and Photoacoustic Imaging for Early Detection and Staging Gynecologic Cancers", Department of Biomedical Engineering, Wayne State University, Detroit, Michigan; corresponding author: mehr@wayne.edu.
(Continued)

*Primary Examiner* — Marjan Fardanesh
(74) *Attorney, Agent, or Firm* — Dinsmore & Shohl, LLP

(57) ABSTRACT

Methods and system are described for multi-parametric, non-invasive, and real-time assessment of blood perfusion and oxygenation in the fetal brain during labor and delivery of a fetus through a vaginal birth canal of a maternal pelvis, and include positioning a probe device in the maternal pelvis during active labor, transmitting and receiving a plurality of ultrasound (US) and photoacoustic (PA) signals between the probe device and fetal brain, displaying in real-time on an US machine communicatively coupled to the probe device one or more images of venous and arterial blood flow of respective blood vessels in the fetal brain, measuring oxygen saturation of the respective venous and arterial blood vessels based on data from the one or more images, and estimating the oxygen measurement in the fetal brain during active labor based on the measured oxygen saturation.

20 Claims, 9 Drawing Sheets

(51) Int. Cl.
   *A61B 8/12* (2006.01)
   *A61B 5/00* (2006.01)
   *A61B 5/1464* (2006.01)

(52) U.S. Cl.
   CPC .......... *A61B 5/4064* (2013.01); *A61B 8/0808* (2013.01); *A61B 8/12* (2013.01); *A61B 5/1464* (2013.01); *A61B 5/4362* (2013.01); *A61B 8/0891* (2013.01); *A61B 8/488* (2013.01); *A61B 2503/02* (2013.01)

(56) References Cited

U.S. PATENT DOCUMENTS

| | | |
|---|---|---|
| 8,108,022 B2 | 1/2012 | Balberg et al. |
| 9,380,967 B2 * | 7/2016 | Esenaliev .......... A61B 5/14542 |
| 2002/0137996 A1 | 9/2002 | Chung et al. |
| 2011/0118576 A1 | 5/2011 | Eghtesady et al. |

OTHER PUBLICATIONS

Hochberg, et al, "Continuous Intrapartum Fetal Scalp Tissue pH and ECG Monitoring by a Fiberoptic Probe", International Biomedics,Inc., Bothell, Washington 98021, pp. 72-85.

Giffei, et al., "First Experience with Continuous pH Measurements on Fetus During Delivery", Archives of Gynecology, J.F. Bergmann Verlag 1978, Arch. Gynecol. 226, 133-136 (1978).

Helwig, et al. "Umbilical cord blood acid-base state: What is normal?", Jun. 1996, Am J. Obstet Gynecol, vol. 175, No. 6, pp. 1807-1814.

Herbst., et al., "Risk Factors for Acidemia at Birth", From the Department of Obstetrics and Gynecology, University Hospital, University of Lund, Lund, Sweden, vol. 90, No. 1, Jul. 1997, pp. 125-130.

Kitlinski, et al., "Gestational Age-Dependent Reference Values for pH in Umbilical Cord Arterial Blood at Term", vol. 102, No. 2 Aug. 2003, by the American College of Obstetricians and Gynecologists, Published by Elsevier, pp. 338-345.

Wang, et al., "Noninvasive Imaging of Hemoglobin Concentration and Oxygenation in the Rat Brain Using High-Resolution Photoacoustic Tomography", Journal of Biomedical Optics, Mar./Apr. 2006. vol. 11(2).

Wang. et al., "Noninvasive Reflection Mode Photoacoustic Imagng Through Infant Skull Toward Imaging of Neonatal Brains", Journal of Neuroscience Methods 168 (2008) 412-421.

Zhang, et al., "Imaging of Hemoglobin Oxygen Saturation Variations in Single Vessels in Vivo Using Photoacoustic Microscopy", Applied Physics Letters ; http://scitation.aip.org/content/aip/journal/apl/90/5?ver=pdfcov.

Rajian, et al.,"Quantitative Photoacoustic Measurement of Tissue Optical Absorption Spectrum Aided by an Optical Contrast Agent", National Institute of Health, Opt Express Mar. 16, 2009, 17(6): 4879-4889.

E. Wilberg-itzel., et al., "Determination of pH or Lactate in Fetal Scalp Blood in Management of Intrapartum Fetal Distress: Randomised Controlled Multicentre Trial", BMJ Research, p. 1-7.

* cited by examiner

ULTRASOUND AND PHOTOACOUSTIC SYSTEMS AND METHODS FOR FETAL BRAIN ASSESSMENT DURING DELIVERY

CROSS REFERENCE TO RELATED APPLICATIONS

The present specification claims priority to U.S. Provisional App. No. 62/451,392, filed Jan. 27, 2017, and entitled "ULTRASOUND AND PHOTOACOUSTIC SYSTEMS AND METHODS FOR FETAL BRAIN ASSESSMENT DURING DELIVERY," the entirety of which is incorporated by reference herein.

TECHNICAL FIELD

The present disclosure generally relates to ultrasound (US) and photoacoustic (PA) systems and methods for fetal brain assessment during labor and delivery and, more specifically, to US and PA systems and methods for multi-parametric, non-invasive, and real-time assessment of oxygen consumption in the fetal brain during labor and delivery of a fetus through a vaginal birth canal.

BACKGROUND

Intrapartum hypoxia, or fetal hypoxia, may occur during delivery of the fetus, causing the fetus to be deprived of an adequate supply of oxygen. Intrapartum hypoxia results in a diminished availability of oxygen to body tissues despite adequate perfusion of the tissue by blood. Such a condition may also result in brain damage to the fetus, including short and/or long term neurological complications. Further, such a condition may be life threatening unless prompt actions are taken to restore well-oxygenated blood to the fetus. For example, a fetus suspected of having intrapartum hypoxia may be delivered by an emergency caesarian section rather than through a vaginal birth delivery method. Many cesarean sections are performed, however, without clear documentation of the fetal status. Moreover, a process of clinical evaluation during labor to order such an emergency cesarean, for example, tends to be performed blindly and based on individual clinician experience.

A fetus will be exposed to transient periods of hypoxia during labor, such as during or after uterine contractions, which most fetuses are able to tolerate due to a placental capacity to act as a reservoir of oxygenated blood and to fetal hemoglobin that is able to transport more oxygen than adult blood to the fetus. However, a fetus may have a placental reservoir that is unable to compensate for the hypoxia and the fetus is exposed to uncompensated hypoxia leading to a risk of short and/or long term neurological complications.

A status of a fetus during labor to detect intrapartum hypoxia may be evaluated by continuous monitoring of a fetal heart rate of the fetus (i.e., fetal heart rate monitoring (FHRM)). A fetus seriously affected by intrapartum hypoxia may show changes in the heart rate, though most fetuses mild or moderate explore to intrapartum hypoxia will not be identified through such heart rate monitoring. Another method to monitor for intrapartum hypoxia includes estimating changes in fetal blood gases during labor by collecting fetal scalp blood using a small blade to create a cut in the fetal scalp in an invasive manner. The pH in superficial blood is then able to be directly estimated, though pH values tend to remain stable despite a prolonged exposure to hypoxia. Yet another method to monitor for intrapartum hypoxia includes use of near infra-red spectroscopy (NIRS) to monitor for oxygen changes in the fetal scalp blood during labor. However, despite a strong correlation between NIRS and dioxygen ($O_2$) blood levels, issues may arise through technical and practical restrictions such as a requirement for correct placement and maintenance of a sensor used with NIRS.

However, none of the conventional methods to assess the oxygen levels of a fetus during labor are reliable in estimating changes in oxygen saturation in the fetal blood during labor. Further, the conventional methods are not able to identify early hypoxic changes in the fetus.

Accordingly, alternative systems and methods to monitor a fetus during delivery to assess a metabolic rate of oxygen of the fetus are desired.

BRIEF SUMMARY

According to the subject matter of the present disclosure, a system for fetal brain assessment during delivery may include one or more processors, one or more memory modules communicatively coupled to the one or more processors, an ultrasound machine comprising a display and communicatively coupled to the one or more memory modules, a probe device communicatively coupled to the ultrasound machine, and machine readable instructions stored in the one or more memory modules. The machine readable instructions may cause the system to perform at least the following when executed by the one or more processors: transmit a plurality of (ultrasound) US and (photoacoustic) PA signals (i.e., safe laser excitation pulses) from the probe device toward a fetal brain upon insertion of the probe device into a vaginal birth canal of a maternal pelvis during active labor, wherein the transmitted PA signals comprise short and safe laser pulses configured to be tunable based on a change in wavelength; receive, into the probe device, a plurality of reflected US and PA signals via the probe device; transmit, via the probe device, the received plurality of reflected US and PA signals to the ultrasound machine; generate one or more images of the fetal brain at least partially based on the US and PA signals in real-time; and display the one or more images on the display of the ultrasound machine.

In accordance with one embodiment of the present disclosure, a method for multi-parametric, non-invasive, and real-time assessment of oxygen in the fetal brain during labor and delivery of a fetus through a vaginal birth canal of a maternal pelvis may include: positioning a probe device in the maternal pelvis within a distance range from the fetal brain during active labor, wherein the probe device is communicatively coupled to an ultrasound (US) machine and one or more processors and transmitting a plurality of US and photoacoustic (PA) signals from the probe device toward the fetal brain. The method may further include receiving, into the probe device, a plurality of reflected US and PA signals via the probe device, transmitting, via the probe device, the received plurality of reflected US and PA signals to the US machine, generating one or more images of brain tissue, venous, and arterial blood flow of respective blood vessels in the fetal brain based on the reflected US and PA signals, displaying in real-time the one or more images via the US machine, measuring flow and oxygen saturation of the respective venous and arterial blood vessels based on data from the one or more images, and estimating an oxygen consumption in the fetal brain during active labor based on the measured oxygen saturation.

These and additional features provided by the embodiments described herein will be more fully understood in view of the following detailed description, in conjunction with the drawings.

BRIEF DESCRIPTION OF THE SEVERAL VIEWS OF THE DRAWINGS

The embodiments set forth in the drawings are illustrative and exemplary in nature and are not intended to limit the subject matter defined by the claims. The following detailed description of specific embodiments of the present disclosure can be best understood when read in conjunction with the following drawings, where like structure is indicated with like reference numerals and in which:

DETAILED DESCRIPTION

The present disclosure relates to systems and methods to optimize clinical care of a fetus and mother care in labor during active labor and delivery by providing direct information regarding oxygen saturation in arterial and venous fetal cerebral and/or cortical blood to monitor the fetal status for intrapartum hypoxia. The systems and methods described herein further permit a visualization of fetal brain tissue and vessels to estimate blood flow and global oxygen consumption in the visualized fetal brain vessels. Further, the systems and methods described herein provide for an estimation of blood movements as a proxy of regional blood perfusion and direction an ultrasound (US) visualization of a pose (i.e., position and orientation) of a head of the fetus in the maternal pelvis during active labor and delivery.

Figure 1:
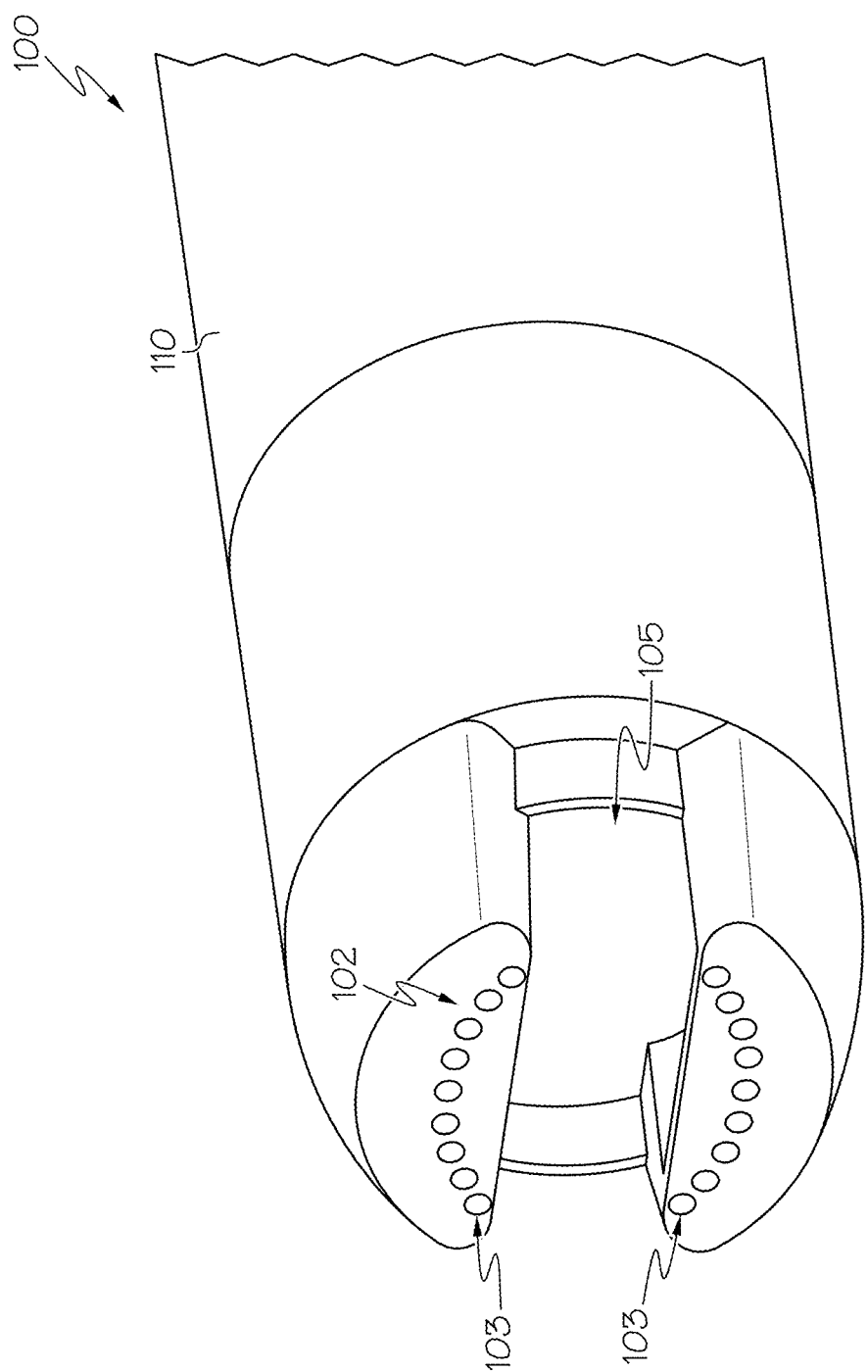
FIG. 1 illustrates an isometric view of a sheath of a ultrasound (US) and photoacoustic (PA) device for fetal brain assessment during delivery, incorporating aspects of the present disclosure.
Figure 2:
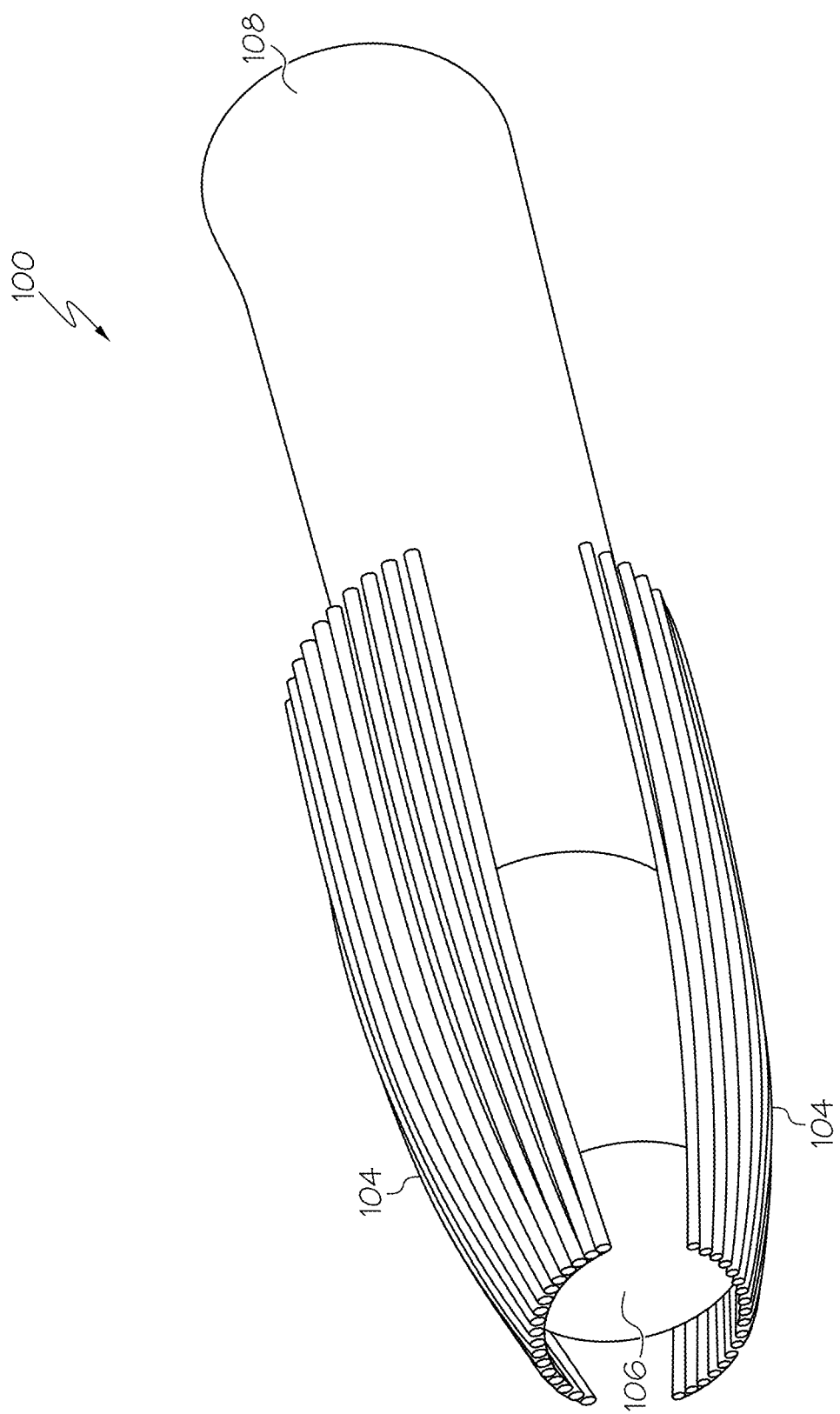
FIG. 2 is an example probe and fiber assembly of a US probe of the US and PA device of FIG. 1 including a surrounding fiber optic alignment assembly, the example probe and fiber assembly configured for placement in the sheath of FIG. 1, and incorporating aspects of the present disclosure.

Referring initially to FIGS. 1-2, a probe device 100 illustrated for assessment of the an oxygen measurement in the fetal brain during labor and delivery of a fetus. For example, as will be described in greater detail below, the oxygen measurement may be of a metabolic rate of oxygen and/or of a global brain oxygen consumption parameter. The probe device 100 includes a sheath 110 including a fiber holder 102. The fiber holder 102 includes a plurality of openings 103 sized and shaped to receive corresponding fibers of fiber assembly 104. The sheath 110 of the probe device includes an opening 105 sized and configured to receive a transvaginal, ultrasound (US) transducer 108 (FIG. 2), which includes an active surface 106. As a non-limiting example, the US transducer 108 may be a curved-array transducer with a frequency range bandwidth of about 5 MHz to about 9 MHz, such that pulses of a frequency in the range may be emitted from an array of about 128 transducer elements. In embodiments, the sheath 110 may include at least two interlocked layers to lock the sheath 110 of FIG. 1 with the assembly of FIG. 2 including the US transducer 108 and the fiber assembly 104. Through such an interlocking, fibers from the fiber assembly 102 may be removed and sterilized. For example, the fibers may be removed after use of the probe device 100 as described herein and prior to repositioning for future use. Other forms of light delivery such as fused fibers (to a customized shape) may also be incorporated into the sheath 110 for light delivery.

US probes are transmitted in a non-ionizing manner through the active surface 106 of the US transducer 108 of the probe device 100, which is communicatively coupled to an US machine. As a non-limiting example, the US probes may be high-frequency probes. The active surface 106 of the US transducer 108 collects the sound waves that bounce back to create images from the sound waves received through the active surface 106. For example, the US transducer 108 records changes in a pitch and direction of the bounced-back acoustic waves to measure and display these waves as a real-time image on a monitor of a computer or US machine, for example.

Doppler US may be used to allow visualization and evaluation of blood flow through arteries and veins of a fetal brain 306 as described herein. Doppler US measures a direction and speed of blood cells moving through blood vessels that cause a change in pitch of the reflected sound waves. A computer may collect and process the reflected sound waves to create graphs or color pictures that are representative of blood flow through blood vessels. Three types of Doppler US include Color Doppler US using a computer to convert Doppler measurements into an array of colors that show a speed and direction of blood flow through a blood vessel, Power Doppler US that is able to provide a greater detail than Color Doppler US such as when blood flow is minimal though does not provide detail regarding blood flow direction, and Spectral Doppler US that displays blood flow graphically in terms of distance traveled per unit of time and that may convert blood flow information into a distinctive sound per heartbeat. Further, Doppler data may be used to estimate blood perfusion parameters such as blood flow in a blood vessel and fractional moving blood volume (FMBV), which are described in greater detail below.

The fiber holder 102 is sized and configured to contain a fiber assembly 104 including a plurality of optical fibers for use in photoacoustic (PA) imaging. The fiber assembly 104 may be formed of fused fiber bundles made of flexible small core silica optical fibers that are fused on proximal and distal ends to create highly flexible fiber bundles that are efficient in transporting laser energies. As a non-limiting example, the fibers may have respective cores of about 100 μm. As fiber core size may change dependent on a type of fiber being used, fibers having different core sizes are within the scope of this disclosure. The bundle of fibers may include multiple fiber optics. As another non-limiting example, the bundle of fibers may include nineteen (19) fibers having a large-core (for example, 1000 μm), the fibers being silica core, polymer cladding fibers. Eighteen (18) fibers of this bundle may be used for light delivery, and one (1) fiber may be use for real-time energy measurement purposes. The fiber assembly 104 may be configured to transmit laser pulses in a uniform distribution of light from optical fibers configured in a curved formation about respective and opposing curved sleeves of the US transducer 108. The fiber assembly 104 is positioned and oriented in the fiber holder 102 of the sheath 110 in a manner to hold fibers in pre-set locations to have an orientation that optimizes light delivery. In a non-limiting example, a focal plane for light delivery may be 2.5 cm away from a distal end of a fiber bundle, and the focal plane may be aligned with a probe image plane at 2.5 cm. It is to be understood that the distance for the focal plane may be adjustable depending on, for example, the dimensions and design of the probe device 100.

A gap formed between the curved sleeves and in front of the active surface 106 of the US transducer 108 may be filled in a contact gel. The contact gel may be made out of material that also acts as a light diffuser (for example, a custom-built gelatin or ultrasound transparent material mixed with light scatterers such as cellulose) to enhance the uniform illumination which is beneficial in Photoacoustic imaging. The sheath 110 of the probe device 100 includes the fiber holder 102 and is disposed about the US transducer 108. The sheath 110 may be a biocompatible fiber holding sheath. For example, the sheath 110 may be a fiber holding sheath made from a medical-grade plastic or like material. As non-limiting examples, the sheath 110 may have a total diameter of 29 mm, and the sheath 110 may be 3D printed using a high resolution printer and bio-compatible material.

In PA imaging, non-ionizing laser pulses and/or radio-frequency (RF) pulses may be used (as in thermoacoustic imaging) and are delivered to biological tissue, and a portion of the delivered energy is absorbed into the tissue and converted to heat that leads to a transient thermoelastic expansion and wideband ultrasonic emission. The US transducer 108 detects the generated ultrasonic waves that are analyzed to produce images. Optical absorption through PA imaging is associated with physiological properties such as hemoglobin concentration and oxygen saturation. The PA signal (i.e., the magnitude and/or frequency of the ultrasonic emission) is proportional to a local energy deposition to reveal physiologically specific optical absorption contrast and thus assist to form 2D or 3D images of targeted areas. As blood typically has higher absorption in order of magnitude than surrounding tissue, a sufficient endogenous contrast exists for PA imaging to visualize blood vessels.

Further, the optical absorption in tissue may be due to endogenous molecules such as hemoglobin. Hemoglobin is an iron-containing oxygen-transport metalloprotein in red blood cells which carries oxygen from respiratory organs to the tissues of the rest of the body where oxygen is released to permit aerobic respiration and provide metabolic energy. Oxy-hemoglobin refers to hemoglobin saturated with oxygen, and deoxy-hemoglobin refers to hemoglobin desaturated with oxygen. Thus, as the absorption spectra of oxy-hemoglobin and deoxy-hemoglobin differ, the difference is able to be used for a measurement of an amount of oxygen in targeted blood vessel to, for example, determine an oxygen saturation measurement.

As will be described in greater detail below with respect to an imaging system 600 of FIG. 8A, or an imaging system 650 of FIG. 8B, the probe device 100 is communicatively coupled to a US machine to monitor and measure cerebral oxygenation during labor and delivery through utilizing information obtained by transvaginal US imaging (such as structure and movement of the blood vessels in the brain and blood flow through the vessels due to real-time US image capture) in combination with oxy-hemoglobin and deoxy-hemoglobin concentrations obtained by PA imaging to provide real-time measurements of arterial and venous oxygen saturation that may be used to estimate a metabolic rate of oxygen consumption in the fetal brain.

Figure 9:
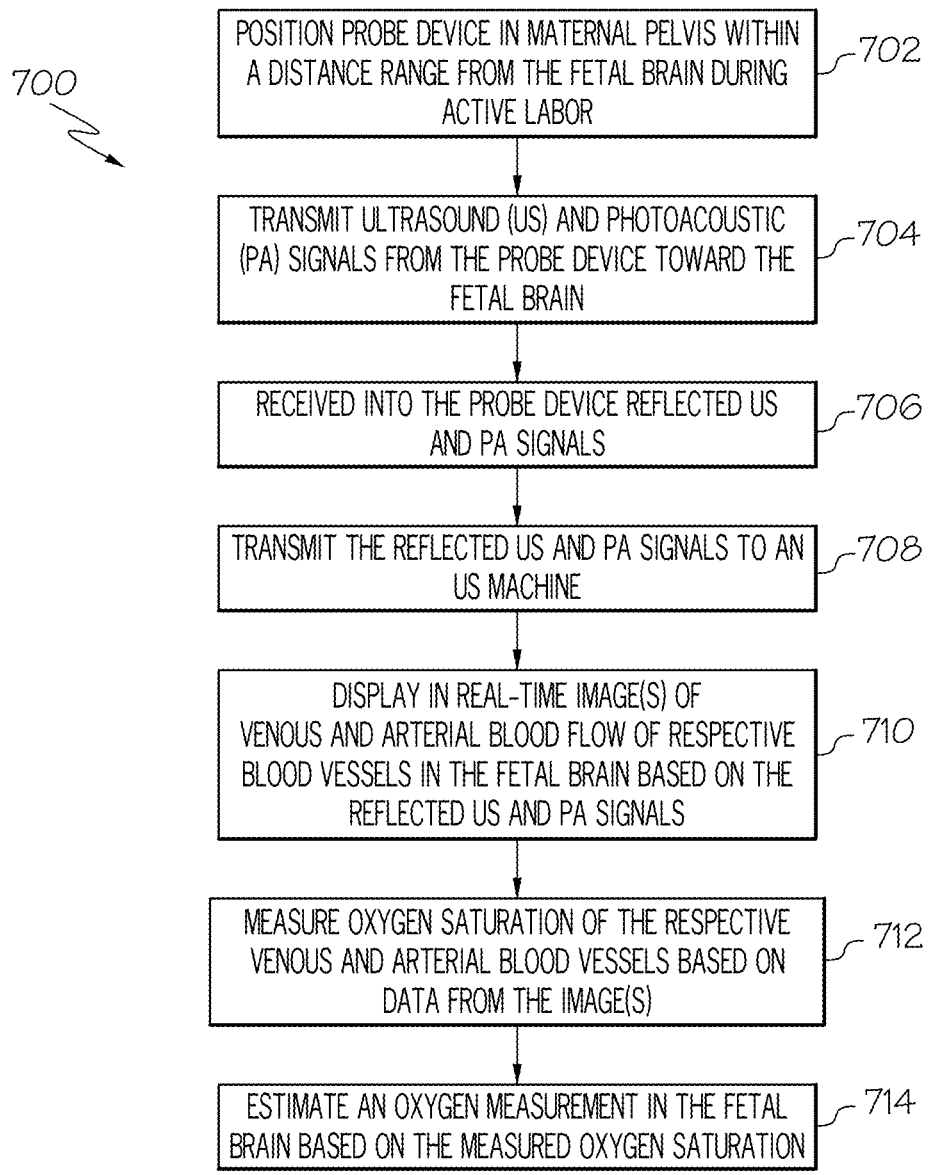
FIG. 9 schematically illustrates a flow chart of a process for utilizing the systems of FIGS. 8A-8B, according to one or more embodiments shown and described herein.

FIG. 9 illustrates a process 700 including a step 702 to position the probe device 100 in the maternal pelvis within a distance range of the fetal brain 306 during active labor. For example, referring to FIG. 3, the probe device 100 is inserted into the vaginal birth canal 302 of a maternal pelvis 200 of a birthing mother during active labor and delivery to be placed near a head of a fetus 304 engaged in the maternal pelvis 200, such as entering into or in the vaginal birth canal 302 during labor. Referring again to FIG. 9, in step 704, US and PA signals are transmitted from the provide device 100 toward the fetal brain 306. In step 706, reflected US and PA signals are received back into the probe device 100, which transmits the reflected US and PA signals to a US machine for processing and to display one or more images. For example, a pair of images may be generated and displayable in parallel, each image generated at least at least partially based on respective US and PA signals in real-time. Additionally or alternatively, an interleaved (and overlaid) image of the fetal brain is generated at least partially based on the US and PA signals in real-time. For example, transmitted US signals may be in the form of US pulses, and PA signals may be in the form of tunable laser pulse signals. In a non-limiting example, while a PA frame rate may be limited to laser pulse repetition, the system described herein is able to achieve a high frame rate. In step 710, the image(s) are displayed in real-time (or pseudo real-time) of venous and arterial blood flow of respective venous and arterial blood vessels in the fetal brain 306 based on the reflected US and PA signals, as described in greater detail further below. For example, the interleaved image and/or the separate images are displayed via the US machine on a display of the US machine. In embodiments, the interleaved image includes an image generated by one of the US signals or the PA signals that is overlaid or superimposed on another image generated by the other of the US signals or the PA signals. Each image may be configured to be adjusted to have similar dimensions to one another prior to generation of the interleaved image such that image dimensions of the resulting superimposed image match and/or are set within a predetermined range of one another.

Figure 4:
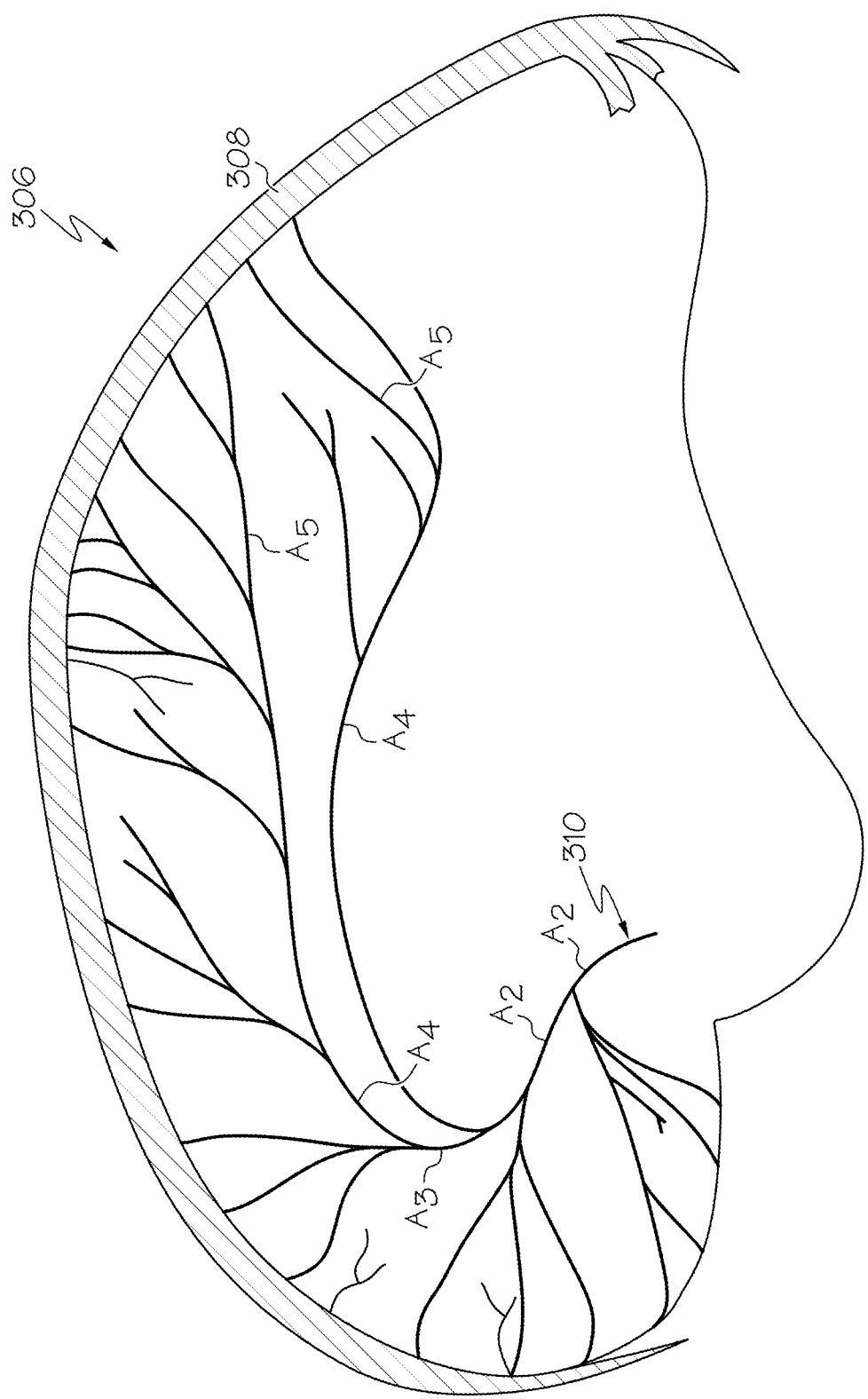
FIG. 4 is a schematic side elevation view of artery and vein portions of the fetal brain of the fetus of FIG. 3.
Figure 5:
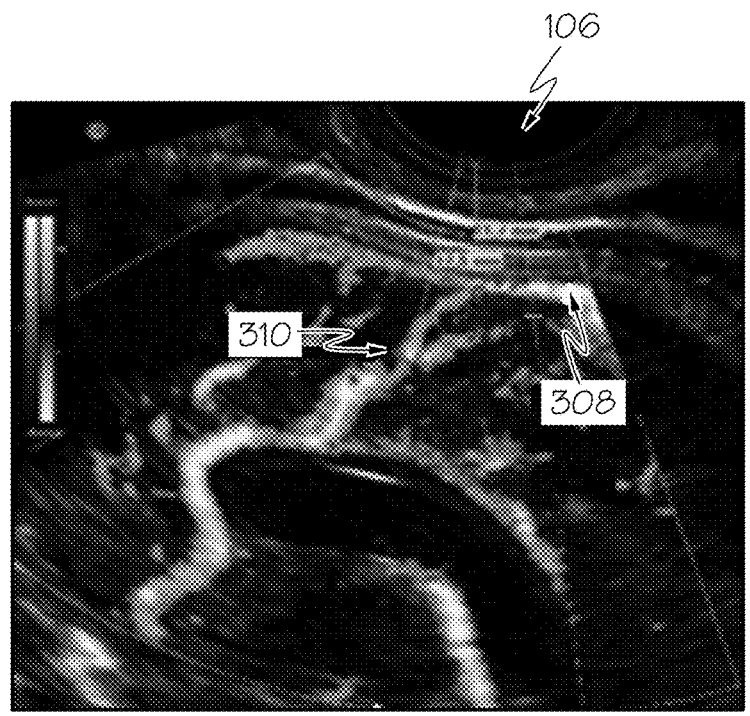
FIG. 5 is an example image of a Doppler ultrasound of a brain (vasculature) obtainable through use of the device of FIG. 1 and illustrating arteries and vein portions of the brain, according to aspects of the present disclosure.

The probe device 100 as inserted is thus able to be used for PA imaging through the fiber assembly 104 and for US imaging through use of the active surface 106 of the US transducer 108 to provide one or more images of the fetal brain 306 of the fetus 304. The one or more images of the fetal brain 306 may include images of one or more veins, such as a superior sagittal sinus 308 of the fetal brain 306 and one or more arteries, such as an anterior cerebral artery 310, as shown in FIGS. 4-5. For example, a non-ionizing light delivery for PA imaging through the fiber assembly 104 is optimized to reach a high penetration depth sufficient to measure blood flow and oxygenation in both the superior sagittal sinus 308 and in arterial cortical branches of the anterior cerebral artery 310 in the fetal brain 306. Thus, the probe device 100 assists to measure oxygen extraction in the fetal brain 306 during active labor and delivery through an ability to measure blood oxygen in both arterial and venous systems as well as brain tissue (including capillary bed for oxygen exchange) of the fetal brain 306. As will be described in greater detail further below, in step 712, oxygen saturation of the respective venous and arterial blood vessels is measured based on data from the interleaved image. Further, in step 714, a metabolic rate of oxygen in the fetal brain 306 is estimated at least partially based on the measured oxygen saturation values.

The venous blood vessel of the fetal brain 306 that is measured includes a portion of the superior sagittal sinus 308. The superior sagittal sinus 308 is an unpaired venous area along an attached margin of the falx cerebri of the fetal brain 306 that allows blood to drain from lateral aspects of the anterior cerebral hemispheres into a confluence of sinuses. Further, cerebrospinal fluid drains into the superior sagittal sinus 308 and is returned to venous circulation.

The arterial blood vessel of the fetal brain 306 that is measured may include one or more portions of arteries in the fetal brain 306. In embodiments, the arterial blood vessel of the fetal brain 306 that is measured includes one or more portions of the anterior cerebral artery 310. The anterior cerebral artery 310 in the fetal brain 306 supplies oxygenated blood to most of the midline portions of the frontal lobes and superior medial parietal lobes of the fetal brain 306. A pair of anterior cerebral arteries arise from an internal carotid artery as part of the circle of Willis in the fetal brain 306, with the left and right anterior cerebral arteries connected together by an anterior communicating artery. The anterior cerebral artery 310 includes five segments $A_1$-$A_5$, with four of those segments ($A_2$-$A_5$) shown in FIG. 5. The first segment $A_1$ is the one that originates from the internal carotid artery and extends into the anterior communicating artery. The second segment $A_2$ extends from the anterior communicating artery to form the pericallosal and callosomarginal arteries. The third segment $A_3$ is also termed the pericallosal artery and is one of the main terminal branches of the anterior cerebral artery 310. The smaller branches of the anterior cerebral artery 310 as shown in the $A_4$-$A_5$ segments are the callosal arteries. For example, a commonly present terminal branch of the anterior cerebral artery 310 bifurcating from the pericallosal artery (i.e., third segment $A_3$) is the callosal marginal artery (i.e., the fourth and fifth segments $A_4$-$A_5$).

Figure 3:
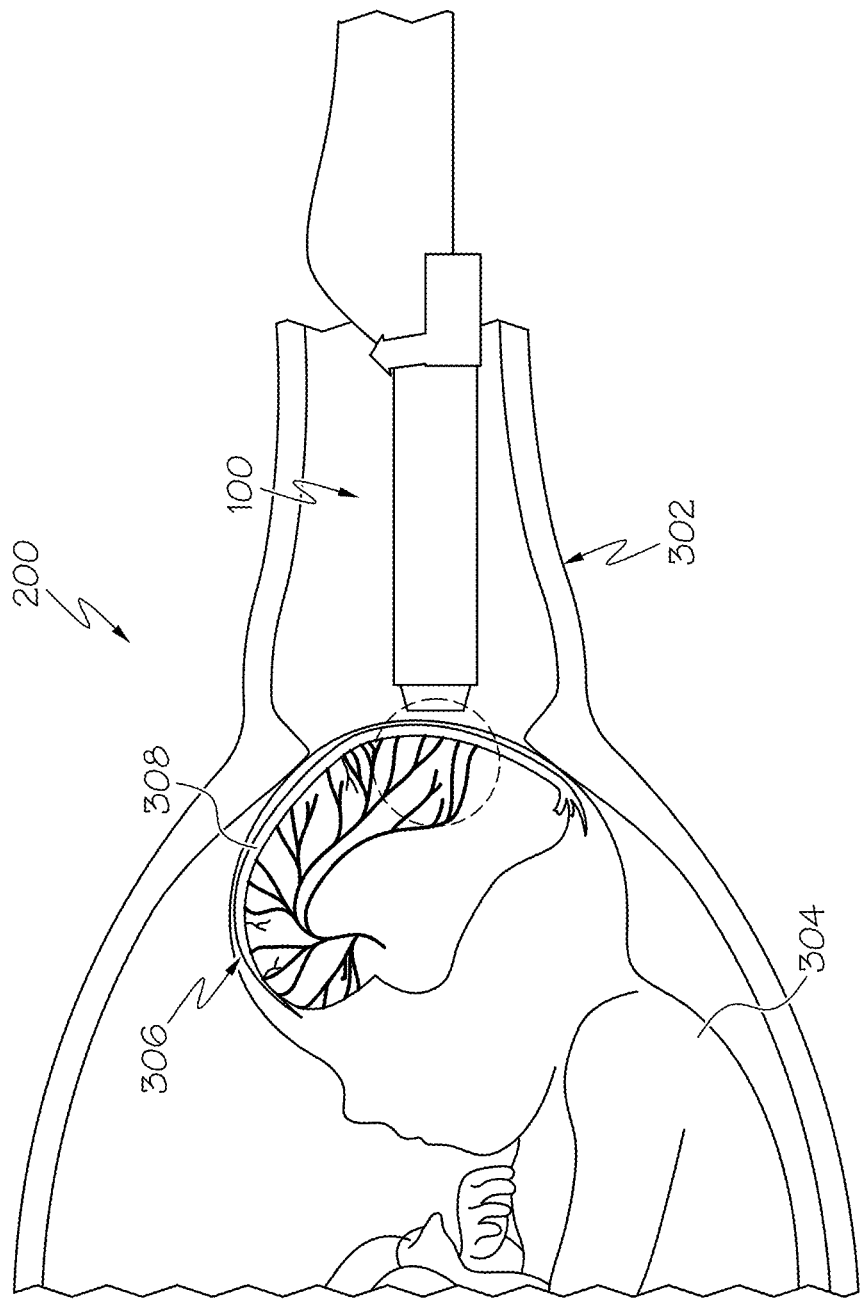
FIG. 3 is a schematic side elevation view of a delivery of a fetus and use of the US and PA device during the delivery to assess the fetal brain, and incorporating aspects of the present disclosure.

When the probe device 100 is inserted in the vaginal birth canal 302 as shown in FIG. 3, it may be positioned at a close distance away from a fontanelle opening of the fetal brain 306 of the fetus 304. In embodiments, the probe device 100 may image the brain through the fontanelle as well as through the fetus skull and scalp. The active surface 106 in combination with the fiber assembly 104 may produce an image as shown in FIG. 5 from the acquired US and PA signals from the fetal brain 306 through the fontanelle opening with use of the US transducer 108 of the probe device 100 through the active surface 106. The US data forms a structural image of the fetal brain 306 that indicates a location and anatomy of the vasculature. For example, the image of FIG. 5 shows the superior sagittal sinus 308 and the anterior cerebral artery 310 of the fetal brain 306. As a non-limiting example, the image of FIG. 5 is an US/Color Doppler image of the fetus 304 indicating a close proximity between the probe device 100 and the superior sagittal sinus 308 and arterial blood flow such as through the anterior cerebral artery 310 of the fetal brain 306. For example, the active surface 106 of the probe device 100 is at a distance of about 11.7 mm from the superior sagittal sinus 308 and at a distance of about 17.5 mm from the anterior cerebral artery 310.

The probe device 100 is able to provide a large field of view of the fetal brain 306 of the fetus 304 through US and PA imaging of the fetal brain 306 during labor with a low depth of superficial sagittal sinus and arterial blood flow through such close proximity to the superior sagittal sinus 308 and the anterior cerebral artery 310 of the fetal brain 306. For example, the active surface 106 of the probe device 100 may be at a distance of less than 25 mm from the superior sagittal sinus 308 and from the anterior cerebral artery 310. In embodiments, the active surface 106 of the probe device 100 may be at a distance of equal to or greater than 25 mm from the superior sagittal sinus 308 and from the anterior cerebral artery 310.

Use of the probe device 100 with a system to provide such US and PA imaging as illustrated in FIG. F allows for a multi-parametric, non-invasive, and real-time assessment of the metabolic rate of oxygen in the fetal brain 306 during labor and delivery of the fetus 304 through a vaginal birth canal 302. Doppler US and US flow information may be obtained through tuning of pulse-echo parameters in a US scanner. PA signals representative of acoustical signals generated by tissue in response to ultrashort laser pulses in, for example, a nanosecond range, may convey information about optical absorption properties of the tissue. While PA signals may be acquired and treated similarly to US echo signals, they are able to provide different information with respect to tissue absorption characteristics such a differential between oxy-hemoglobin and deoxy-hemoglobin in the blood vessels associated with the tissue. For example, difference between the optical absorption spectrums of oxy-hemoglobin and deoxy-hemoglobin enable spectroscope PA technology, which represents a PA signal as two or more wavelengths, to measure respective concentrations of oxy-hemoglobin and deoxy-hemoglobin and thus provide a blood oxygen saturation ($SO_2$). Light wavelengths to measure $SO_2$ may be below 900 nm, for example, and thus a mobile and compact laser(s) with an embedded cooling system may be utilized with the probe device 100.

Figure 6:
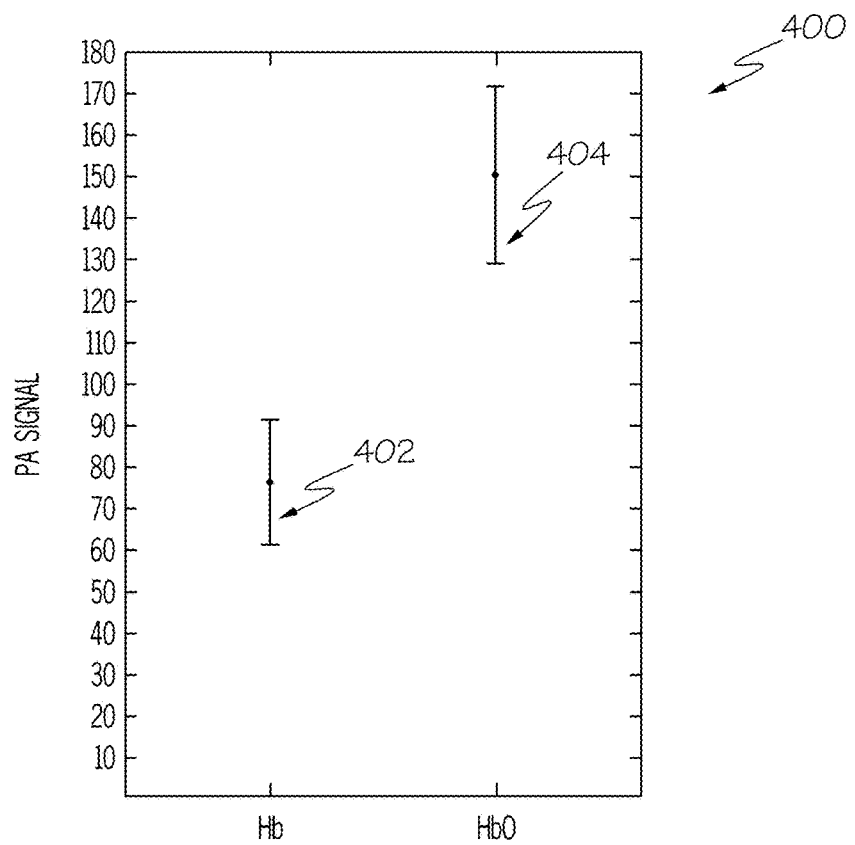
FIG. 6 is an example graph of PA signal difference between oxy-hemoglobin and deoxy-hemoglobin Hb at 532 nm wavelength, according to aspects of the present disclosure.

FIG. 6, for example, illustrates a chart 400 depicting the PA signal difference between oxy-hemoglobin (HbO) and deoxy-hemoglobin (Hb) at 532 nm wavelength when measured by the probe device 100. A result 402 shows a range of PA signals (i.e., from about 60 to 90 pixel values) associated with oxy-hemoglobin, and a range 404 shows a higher range of PA signals (i.e., from about 130 to 170 pixel values) associated with deoxy-hemoglobin. FIG. 6 is an example from an experiment in which images were displayed on a screen using a 256 level color map, and the values from the chart of PA signals are representative of pixel values in a range of about 0 to 255. Additional detail regarding the system including, but not limited to, an associated architecture of the system and a comparison between oxygen saturation measurements through PA and gold-standard blood gas analyzer is provided in an Appendix A in U.S. Provisional App. No. 62/451,392, to which the present disclosure claims priority and which is incorporated in entirety by reference herein and above.

The acoustic signals from respective US echoes and PA laser pulses may be acquired by a US machine that is communicatively coupled to the probe device 100 in an imaging system, and the probe device 100 may be enabled to control a transmit/receiving timing of the signals to synchronize the US machine with the PA laser pulses to acquire interleaved US and PA images on a graphical user interface of the US machine. For example, an imaging sequence may be on the US machine to acquire and provide real-time US and PA frames for simultaneous display on the graphical user interface of the US machine. The interleaved image may be displayed as an image of the fetal brain 306 including an image of blood vessels such as respective the venous and arterial blood vessels of a superior sagittal sinus 308 and one or more portions of an anterior cerebral artery 310 within the fetal brain 306.

Further, the imaging system enables access to pre-processed radio-frequency (RF) data for an implementation of customized signal processing and image formation algorithms. By combining US, US Doppler, and PA information, measurements such as arterial and venous oxygen saturation and a differential between arterial and venous oxygen saturation of the fetal brain 306 may be obtained. For example, a first measurement of oxygen saturation may be determined for a first section of the superior sagittal sinus 308 from the image(s) based on a PA signal difference between oxy-hemoglobin and deoxy-hemoglobin values at the first section. Further, a second measurement of oxygen saturation may be determined for a second section of the one or more portions of an anterior cerebral artery 310 from the image(s) based on a PA signal difference between oxy-hemoglobin and deoxy-hemoglobin values at the second section. A differential between arterial and venous oxygen saturation of the fetal brain may be determined based on the determined first and second measurements of oxygen saturation.

In embodiments, information may be obtained from the US data and/or US image(s) including a location of brain tissue, and location and sizes of arterial and venous blood vessels within a cortex of the fetal brain. Further, information may be obtained from the PA data and/or PA image(s) including blood arterial and venous flow including oxygen saturation ($SO_2$) within accessible areas of the cortex. Oxygen saturation is defined as a ratio of oxy-hemoglobin to total hemoglobin (oxy-hemoglobin plus deoxy-hemoglobin) and may be found in areas of the cortex that are accessible by the probe device 100 up to a couple of centimeters of depth based on PA light penetration by the fiber assembly 102. From these measurements, measurements such as oxygen saturation in fetal brain tissue and blood flow in the anterior cerebral artery (ACA) 310 may be obtained. The measurement of oxygen saturation in the fetal brain tissue may be an oxygen measurement that is indicative of an oxygen extraction factor or a blood oxygen exchange rate within the brain tissue. The blood flow in the ACA 310 measurement is representative of tissue perfusion and is based on the PA information retrieved from the probe device 100 to determine an estimated fractional moving blood volume (FMBV) for the ACA 310. The FMBV, for example, and as described in greater detail below, is estimated using power Doppler US (PDU) in a cerebral cortical area, where cerebral blood oxygen saturation is also measured through signals obtained from the probe device 100 as described herein. Blood flow in the superior sagittal sinus (SSS) 308 may similarly be obtained from the PA information to determine the FMBV for the SSS 308. A global brain oxygen consumption parameter may be determined as a parameter that is based on the determined oxygen saturation and determined FBMV values for each of the ACA 310 and the SSS 308. The global brain oxygen consumption parameter may determined as shown in Equation 1 below as an approximate, proportional value to a value determined by the right hand side of Equation 1:

Global Brain Oxygen Consumption≈$[(SO_2)_{ACA}-FMBV_{ACA}]-[(SO_2)_{SSS}-FMBV_{SSS}]$ (Equation 1)

Oxygen saturation values may be extracted through a spectroscopic PA (sPA) method in which an amplitude of a PA signal is proportional to an optical absorption of absorbers including oxy-hemoglobin and deoxy-hemoglobin. In embodiments, the PA signals are filtered such as through being passed through a Hamming window bandpass filter to localize the signal in a sample holder and minimize spectral leakage. For each signal, a signal amplitude may be computed by integrating an envelope of each signal using, for example, a Hilbert transform. An average and standard deviation of the signal amplitude may further be computed.

The PA signals may be analyzed to determine correlation maps and a blood oxygen saturation map. Both maps are based on extinction coefficients. The correlation maps include an oxygenation correlation map (OCM) and a deoxygenation correlation map (DOCM). The OCM may be determined based on a correlation between a known absorption of oxy-hemoglobin (HbO) and a recorded PA signal, and the DOCM may be determined based on a correlation between a known absorption of deoxy-hemoglobin (Hb) and the recorded PA signal. The result may be normalized, and a 256 levels color map may be applied on the normalized result. Determination of the correlation maps assists with determining the extinction coefficients. Equation 2 below sets for an equation to calculate oxygen saturation in blood:

$$SO_2 = \frac{[HbO]}{[HbO]+[Hb]} = \frac{PA(\lambda_2)*\varepsilon(Hb,\lambda_1) - PA(\lambda_1)*\varepsilon(Hb,\lambda_2)}{PA(\lambda_1)*\Delta\varepsilon(\lambda_2) - PA(\lambda_2)*\Delta\varepsilon(\lambda_2)}$$ (Equation 2)

In Equation 2 above, $\Delta\varepsilon(\lambda_n)=\varepsilon(HbO,\lambda_n)-\varepsilon(HbO,\lambda_n)$ for each wavelength n and is representative of a difference in the extinction coefficient for each wavelength. The oxygen saturation ($SO_2$) may be calculated for all measured PA signals to generate a percentage value, and more than two wavelengths may be measured. A final oxygen saturation result may be an average of all pairs of PA signals. Similarly, Equation 3 below sets forth another manner to calculate oxygen saturation in blood:

$$SO_2 = \frac{[HbO]}{[HbO]+[Hb]} = \frac{\mu_a^{\lambda_2}*\varepsilon_{Hb}^{\lambda_1} - \mu_a^{\lambda_1}*\varepsilon_{Hb}^{\lambda_2}}{\mu_a^{\lambda_1}*\Delta\varepsilon_{Hb}^{\lambda_2} - \mu_a^{\lambda_2}*\Delta\varepsilon_{Hb}^{\lambda_1}}$$ (Equation 3)

In Equation 3 above, $\mu_a$ is an absorption coefficient measured in inverse centimeters ($cm^{-1}$). Further, $\Delta\varepsilon_{Hb}=\varepsilon_{HbO}-\varepsilon_{Hb}$, and $\varepsilon_{Hb}$ and $\varepsilon_{HbO}$ respectively are known molar extinction coefficients of Hb and HbO measured in inverse cm-M ($cm^{-1}$ $M^{-1}$). Hb and HbO are molar concentrations of, respectively, deoxy-hemoglobin and oxy-hemoglobin.

Another parameter, a cerebral metabolic rate of oxygen ($CMRO_2$), may be estimated at least partially based on the obtained measurements of arterial and venous oxygen saturation and a differential between arterial and venous oxygen saturation of the fetal brain 306. $CMRO_2$ is a rate of oxygen consumption by the fetal brain 306 that has a direct relationship with a structural and functional development of the fetal brain 306.

For example, the probe device 100 is used to obtain a direct measurement of oxygen saturation in the arterial and venous fetal cerebral blood. While Intrapartum Fetal Heart Rate Monitoring (IFHRM) in a method of care in monitoring fetal hypoxia during labor through which a transabdominal Doppler US is used to monitor the fetal heart rate as an abnormal IFHRM finding has been associated with intrauterine hypoxia, IFHRM is not a direct estimator of blood oxygenation. Thus, most fetuses that are delivered by cesarean section due to an abnormal IFHRM finding do not show reduced oxygen levels in umbilical cord blood. Further, fetuses with truly low oxygen levels might be identified through heart rate tracing such as through IFHRM alone. Thus, the probe device 100 described herein may be used in addition to or as an alternative of such heart rate tracing methods and other monitoring methods described herein.

Through use of the probe device 100, arterial and venous oxygen concentrations based on PA signals from the probe device 100 may be determined. A differential in arterial and venous oxygen saturation may be determined based on the difference between the determined arterial and venous oxygen concentrations. Further obtained information may include a cerebral blood flow (CBF), described in greater detail below as determined based on a velocity time integral multiplied by a blood vessel area, and a cranial volume. The cranial volume may be obtained from a transabdominal US, from which additional determined parameters may include fetal position and head location, placenta location, amniotic fluid volume, estimated fetal weight, and biparietal diameter and head circumference. The probe device 100 may be used alongside the transabdominal US (and PA) to determine oxygen measurements as described herein.

An oxygen measurement of the cerebral metabolic rate of oxygen ($CMRO_2$) may be determined at least partially based on CBF, and an estimated fractional moving blood volume (FMBV), described in greater detail below, may be determined. Equation 3 below sets forth an example equation to determine $CMRO_2$. In Equation 4 above, 0.2 micromols $O_2$ per hemocrit unit is representative of a capacity of blood to carry oxygen ($O_2$).

$$CMRO_2 = CBF * [(SO_2)_{ACA} - (SO_2)_{SSS}] * \frac{0.2\ micromolsO_2}{hemocrit\ unit} \quad \text{(Equation 4)}$$

Further, the probe device 100 is used to obtain a direct visualization of fetal brain vessels to allow for an estimation of blood flow and global oxygen consumption of the fetal brain 306 during delivery. As a non-limiting example, a system incorporating the probe device 100 is able to evaluate the fetal cerebral metabolic rate of oxygen ($CMRO_2$) during labor by estimating differences in oxygen saturation between arterial and venous blood. For example, pulsed Doppler US may be used to identify cortical arterial branches from the pericallosal and callosal marginal arteries of the anterior cerebral artery 310 and to identify the superior sagittal sinus 308 of the fetal brain 306. The vessels may be delineated using Color Doppler US and the diameters of the vessels may be measured. Parameters for a velocity time integral (VTI) and a vessel diameter may be determined. A vessel area, such as an area of ACA 310 (ACAarea), may be determined from the vessel diameter. The VTI and ACAarea parameters may be used to calculate blood flow through a blood vessel through a formula set forth as VTI*ACAarea. VTI is a velocity time integral that is the integral of all distances traveled by blood cells in a vessel in units of centimeter per second (cm/s: velocity of red blood cells) over time (s) and representative as unites of (cm/s)/s, which may thus be expressed in units of centimeters (cm). The ACA area may be calculated in units of $cm^2$. The formula of VTI*ACAarea determines a volume calculation in units of $cm^3$.

Figure 7:
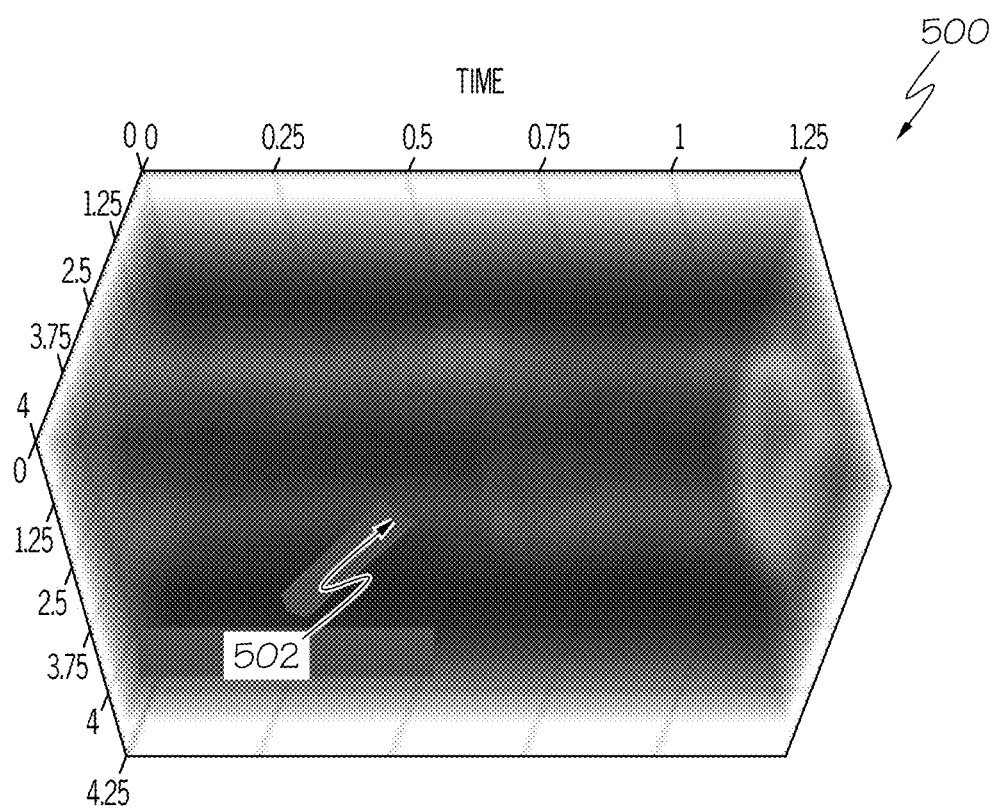
FIG. 7 is an example 3D graph of a blood vessel obtained by the device of FIG. 1 to illustrate a blood flow velocity measurement in time using US Doppler or ultrafast Doppler.

Diameters at a first section of the venous blood vessel and a second section of the arterial blood vessel may be determined, and a respective blood flow velocity measurement through the venous and arterial blood vessels at least partially based on a velocity time integral of the respective first and second sections and the respective determined diameters. For example, FIG. 7 illustrates a three-dimensional (3D) graph 500 of a blood flow velocity measurement in time that is obtainable through using US Doppler or ultrafast Doppler US data for an imaged blood vessel 502 to measure, for example, an estimated fractional moving blood volume (FMBV), described in greater detail further below. The example graph 500 includes time along a z-axis in units of seconds, for example, and blood vessel dimensions on the x-axis and y-axis in units of millimeters. The frame rate of the ultrafast Doppler US maybe up to 3000 frames/second as a non-limiting example, though the frame rate may change depending on imaging depth and other parameters. Global oxygen consumption may be estimated at least partially based on a difference in oxygen concentration between the arterial and venous blood flow.

Additionally, the probe device 100 is used to estimate blood movements of the fetal brain vessels as a proxy of regional blood perfusion. A time-averaged blood perfusion (TABP) may be calculated in cerebral cortex of the fetal brain 306 through using a power Doppler US (PDU) as an indirect estimator of blood perfusion (i.e., as measured through blood flow). For example, TABP is calculated from an intensity of pixels that contain PDU information. The system may utilize a software program including an algorithm to analyze the PDU intensity signals through performing a normalization procedure. The normalization procedure may be used to obtain an estimated fractional moving blood volume (FMBV) corresponding to a set of fetal blood vessels, as described below.

A normalization value (NV) of 1 (indicating a real blood movement of 100%) is assigned to an intensity value that is a selected PDU intensity signal most probably obtained from blood movement as may be automatically defined by the software. All intensities of a set of PDU intensity signals above the NV and having a value greater than the selected PDU intensity signal will be transformed and set to 1. Further, all intensities of a set of PDU intensity signals below the NV and having a value less than the selected PDU intensity signal will be converted into and set as fractions of the NV accordingly. Thus, final averaged estimation ranges of from about 0 to about 1 may be expressed as percentage terms of blood movement of the fetal blood vessels of the fetal brain 306, such as an estimated fractional moving blood volume (FMBV) as an indirect estimation of brain blood perfusion. The TABP is representative of a percentage of blood movement in a defined area of a fetal blood vessel and compensates for external factors such as an effect of depth and tissue interphases in the intensity of the power Doppler signals.

For example, in embodiments, PDU intensity signals are used to estimate fetal blood perfusion and display a strength of returning echoes from the fetal brain to the probe device 100 as described herein and based on a total integrated power for positive and negative velocities. The power of the returning echoes is squared and converted to decibels and displayed in a single color intensity scale. In embodiments, the function may be linear. The PDU intensity signals may be analyzed to determine blood movement for perfusion analysis. For example, the PDU intensity signals may recognize slow blood movement with respect to blood perfusion. Analysis of the PDU intensity signals permits a detection of mild changes in an amplitude of backscattered echoes to identify blood movement in small fetal vessels. Further, quantification of the PDU intensity signals may be performed through an intensity analysis to determine FMBV. In particular, FMBV estimates a fraction of blood in a defined region of interest (ROI). PDU signals originating from blood movement may be analyzes, which signals may be affected by depth, tissue interphases, and velocity within the vessels. In embodiment, a FMBV algorithm identifies a PDU value representative of a true blood movement in a ROI and uses the PDU value for comparison as a normalized value against the other PDU signals, as described above. The normalization may reduce false perspectives based on depth, such as false perspectives of increased perfusion due to high-intensity signals when a structure is located near the probe device 100 or of decreased perfusion due to low-intensity signals when the structure is located farther from the probe device 100.

Through the FMBV algorithm, a ROI may be manually delineated in each image of a fetal brain obtained through PDU and the probe device 100 that illustrate information about blood movement within fetal cerebral vessels. All pixels included in the delineated ROI are analyzed. For example, in a TIF-format image, all pixels may be represented by three numbers that correspond to an amount of red, green, and blue present in a given pixel. For a pixel containing only gray-scale information, intensity values of the three-color channels will be the same. To separate gray-scale images from color pixels, the images may first be read into a software program such as a MATLAB® program. Through the program, the images are separated into three matrices, each containing one of the base colors. Only color pixels are analyzed, and the other pixels are set to zero. In embodiments, a green channel may be selected as a measure of indicated power based on a near linear relationship between an amount of green in a color pixel and a level of displayed power. Green channel intensity values may be plotted in a cumulative distribution, which may present a deflection point (knee) where a power value corresponding to this deflection point may be selected as a suitable normalization value (NV). To establish the NV, a linear fit may be determined for a distribution function that may be rotated such that a best fit falls on the abscissa. A value corresponding to a maximum of the rotated distribution function may represent an initial NV. Further, two tangents may be drawn at points where the linear fit intersects the distribution function, and an intersection of the tangents may provide an alternative NV. A lower of the NV and alternative NV and the initial NV may be set as the first NV. The procedure may then be repeated only including values exceeding the first NV, and a second determined value may be set as a second, final NV that receives a value of 1 and to which all other PDU values are normalized. As described above, all PDU values above the NV are set to 1. A mean of all normalized values may determine the FMBV, which may be multiplied by 100 and expressed as a percentage.

Further, the probe device 100 is used to obtain a direct US visualization of the pose of a head of the fetus 304 in the maternal pelvis 200. Direction visualization of a head of the fetus 304 within the uterus may provide information about the orientation and descent of the fetal head in the maternal pelvis 200 during labor and delivery.

Figure 8A:
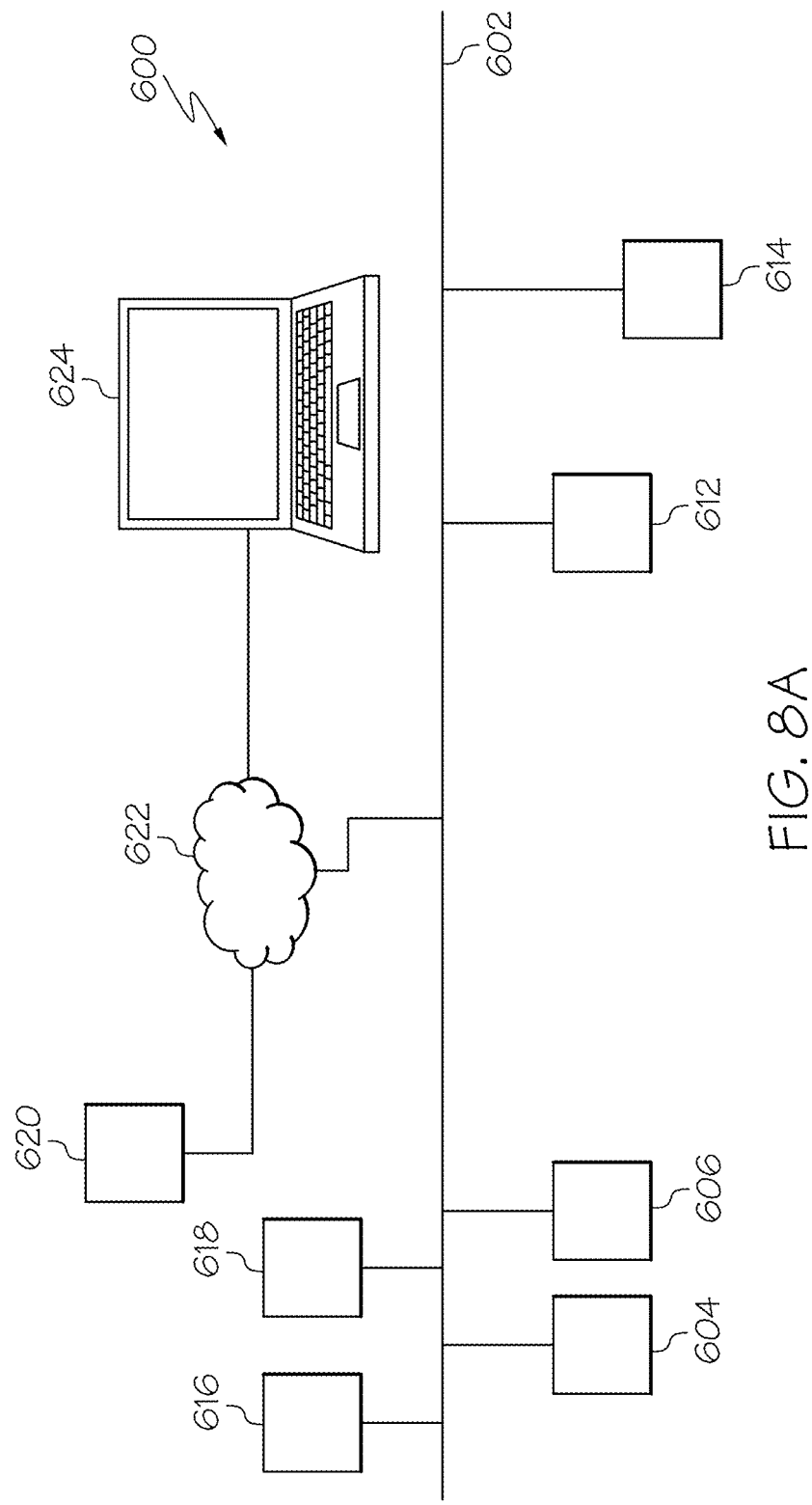
FIG. 8A schematically illustrates an example system for implementing computer and software based methods to utilize the device of FIG. 1, according to one or more embodiments shown and described herein.

In an embodiment, and referring to FIG. 8A, a system 600 may be an imaging system for implementing computer and software-based methods to provide a real-time assessment of a metabolic rate of oxygen in a fetal brain during delivery through use of combined US and PA imaging techniques described herein to predict fetal hypoxia. FIG. 3 illustrates the exemplary system 600 as being implemented along with using a graphical user interface (GUI) displaying a home screen for a user to access the platform and/or view a dashboard as described herein and that is accessible at a user workstation (e.g., a mobile and/or stationary computing device such as a computer 624 that may be an US machine, for example). The system 600 includes a communication path 602, one or more processors 604, a memory component 606, transducer probe device 612 (similar to the probe device 100 described herein), a storage or database 614, an imaging module 616, a network interface hardware 618, a network 622, a server 620, and at least one computer 624. The various components of the system 600 and the interaction thereof will be described in detail below.

While only one application server 620 and one user workstation computer 624 is illustrated, the system 600 can include multiple workstations and application servers containing one or more applications that can be located at geographically diverse locations across a plurality of physical sites. In some embodiments, the system 600 is implemented using a wide area network (WAN) or network 622, such as an intranet or the Internet, or other wired or wireless communication network that may include a cloud computing-based network configuration. The workstation computer 624 may include digital systems and other devices permitting connection to and navigation of the network. Other system 600 variations allowing for communication between various geographically diverse components are possible. The lines depicted in FIG. 8A indicate communication rather than physical connections between the various components.

As noted above, the system 600 includes the communication path 602. The communication path 602 may be formed from any medium that is capable of transmitting a signal such as, for example, conductive wires, conductive traces, optical waveguides, or the like, or from a combination of mediums capable of transmitting signals. The communication path 602 communicatively couples the various components of the system 600. As used herein, the term "communicatively coupled" means that coupled components are capable of exchanging data signals with one another such as, for example, electrical signals via conductive medium, electromagnetic signals via air, optical signals via optical waveguides, and the like.

As noted above, the system 600 includes the processor 604. The processor 604 can be any device capable of executing machine readable instructions. Accordingly, the processor 604 may be a controller, an integrated circuit, a microchip, a computer, or any other computing device (i.e., such as a graphics processing unit (GPU)). The processor 604 is communicatively coupled to the other components of the system 600 by the communication path 602. Accordingly, the communication path 602 may communicatively couple any number of processors with one another, and allow the modules coupled to the communication path 602 to operate in a distributed computing environment. Specifically, each of the modules can operate as a node that may send and/or receive data.

As noted above, the system 600 includes the memory component 606 which is coupled to the communication path 602 and communicatively coupled to the processor 604. The memory component 606 may be a non-transitory computer readable medium or non-transitory computer readable memory and may be configured as a nonvolatile computer readable medium. The memory component 606 may comprise RAM, ROM, flash memories, hard drives, or any device capable of storing machine readable instructions such that the machine readable instructions can be accessed and executed by the processor 604. The machine readable instructions may comprise logic or algorithm(s) written in any programming language such as, for example, machine language that may be directly executed by the processor, or assembly language, object-oriented programming (OOP), scripting languages, microcode, etc., that may be compiled or assembled into machine readable instructions and stored on the memory component 606. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. In embodiments, the system 600 may include the processor 604 communicatively coupled to the memory component 606 that stores instructions that, when executed by the processor 604, cause the processor to perform one or more tool functions as described herein.

Still referring to FIG. 8A, as noted above, the system 600 comprises the display such as a GUI on a screen of the computer 624 for providing visual output such as, for example, US and/or PA imaging and/or associated physiological measurement information based on received US and/or PA signals. The computer 624 may include one or more computing devices across platforms, or may be communicatively coupled to devices across platforms, such as mobile smart devices including smartphones, tablets, laptops, and/or the like.

The GUI may present a user with a home screen, for example, as described herein, which home screen may display one or more views as images provided through the imaging module 616, as described in greater detail above with respect to imaging techniques based on US and/or PA signals obtained from the transducer probe device 612 as described herein. The display on the screen of the computer 624 is coupled to the communication path 602 and communicatively coupled to the processor 604. Accordingly, the communication path 602 communicatively couples the display to other modules of the system 600. The display can include any medium capable of transmitting an optical output such as, for example, a cathode ray tube, light emitting diodes, a liquid crystal display, a plasma display, or the like. Additionally, it is noted that the display or the computer 624 can include at least one of the processor 604 and the memory component 606. While the system 600 is illustrated as a single, integrated system in FIG. 8A, in other embodiments, the systems can be independent systems. As will be described in further detail below, the processor 604 may process the input signals received from the system modules and/or extract information from such signals.

The system 600 includes the network interface hardware 618 for communicatively coupling the system 600 with a computer network such as network 622. The network interface hardware 618 is coupled to the communication path 602 such that the communication path 602 communicatively couples the network interface hardware 618 to other modules of the system 600. The network interface hardware 618 can be any device capable of transmitting and/or receiving data via a wireless network. Accordingly, the network interface hardware 618 can include a communication transceiver for sending and/or receiving data according to any wireless communication standard. For example, the network interface hardware 618 can include a chipset (e.g., antenna, processors, machine readable instructions, etc.) to communicate over wired and/or wireless computer networks such as, for example, wireless fidelity (Wi-Fi), WiMax, Bluetooth, IrDA, Wireless USB, Z-Wave, ZigBee, or the like.

Still referring to FIG. 8A, data from various applications running on computer 624 can be provided from the computer 624 to the system 600 via the network interface hardware 618. The computer 624 can be any device having hardware (e.g., chipsets, processors, memory, etc.) for communicatively coupling with the network interface hardware 618 and a network 622. Specifically, the computer 624 can include an input device having an antenna for communicating over one or more of the wireless computer networks described above.

The network 622 can include any wired and/or wireless network such as, for example, wide area networks, metropolitan area networks, the Internet, an Intranet, satellite networks, or the like. Accordingly, the network 622 can be utilized as a wireless access point by the computer 624 to access one or more servers (e.g., a server 620). The server 620 and any additional servers generally include processors, memory, and chipset for delivering resources via the network 622. Resources can include providing, for example, processing, storage, software, and information from the server 620 to the system 600 via the network 622. Additionally, it is noted that the server 620 and any additional servers can share resources with one another over the network 622 such as, for example, via the wired portion of the network, the wireless portion of the network, or combinations thereof.

Figure 8B:
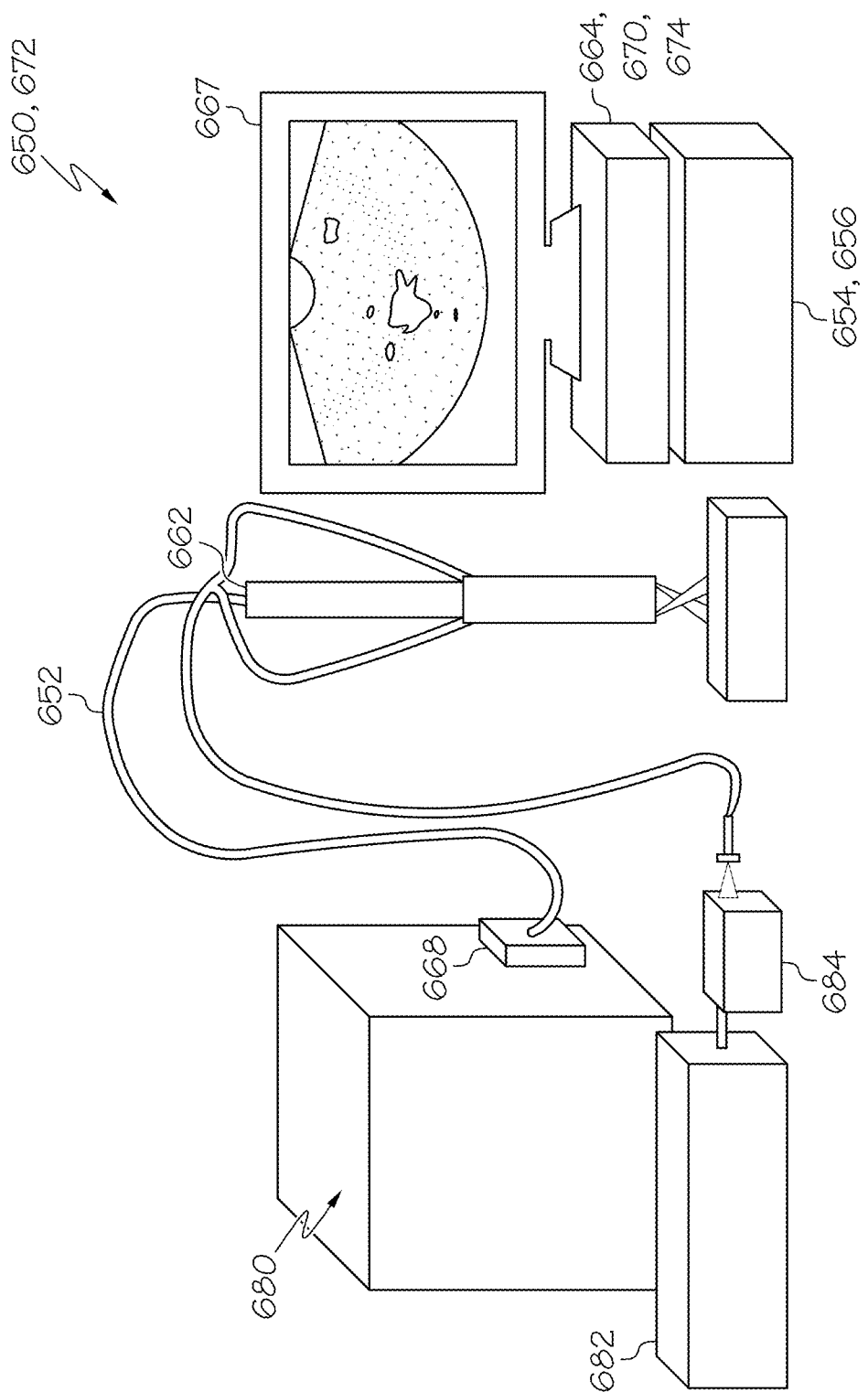
FIG. 8B schematically illustrates another example imaging system for implementing computer and software based methods to utilize the device of FIG. 1, according to one or more embodiments shown and described herein.

In an embodiment, and referring to FIG. 8B, a system 650 may be an imaging system similar to the system 600 with additional described components. The system 650 may include, similar to the system 600, a communication path 652 (similar to the communication path 602), one or more processors 654 (similar to processor(s) 604), a memory component 656 (similar to the memory component 606), a transducer probe device 662 (similar to the transducer probe device 612), a storage or database 664 (similar to the database 614), an imaging module 667 (similar to the imaging module 616), a network interface hardware including components 668 (similar to the network interface hardware 618), a network 672 (similar to the network 622), a server 670 (similar to the server 620), and at least one computer 674 (similar to the computer 624).

Additionally, the system 650 includes an acquisition system 680 communicatively coupled to the transducer probe device 662 through component 688 and wires of the communication path 652. The acquisition system 680 may be communicatively coupled to the computer 674 through either a wired or wireless connection. The acquisition system 680 may be a US real-time data acquisition system including 128 channels.

Further, the one or more processors 654 of the system 650 includes a FPGA based control unit communicatively coupled to a laser 682 and the acquisition system 680. The FPGA may be high speed at about 100 MHz or faster and may be center timing unit in the system 650. The laser 682 is communicatively coupled to an optical parametric oscillator (OPO) 684 that converts an input laser wave with a frequency into two output waves of lower frequency. A laser assembly including the laser 682 and OPO 684 may operator at 30 Hz and utilize real-time pulse energy monitoring. The transducer probe device 662 in FIG. 8B is illustrated as sending signals to (such as tunable laser pulses) and receiving signals from an object schematically disposed below the transducer probe device 662. In embodiments, the system may have two or more lasers (that each may or may not be tunable) that drive all or a sub group of fibers in order to achieve faster spectroscopic PA imaging.

The probe device 100 with use of one or more systems as described herein provides for a direct, accurate, and real-time monitoring blood oxygen saturation in the fetal brain through use of US and PA imaging, including Doppler, to provide measurements such as TABP, blood vessel flow, and oxygen saturation level in the anterior cerebral artery 310 and the superior sagittal sinus 308 of the fetal brain 306. The probe device 100 may be used to provide clinicians to optimize the clinical care of fetuses and birthing mothers during active labor and delivery. For example, the probe device 100 may provide a clinician with an objective set of information of the status of the fetus 304 during labor by providing such direct information on oxygen saturation in arterial and venous cerebral blood and a direct visualization of the associated vessels as described herein to allow for an estimation of blood flow and global oxygen consumption with respect to the vessels. A percentage of blood movement in a studied area of a vessel may be provided and calculated as an indirect estimator of blood perfusion. Further, a US visualization may be provided to present information regarding the pose of the head of the fetus 304 in the maternal pelvis 200 during delivery.

Measurements by the probe device 100 may be based on US and PA images from recordings that are performed after rupture of membranes in women with active labor, such as women at about a greater than 2 cm dilation with active uterine contractions. In embodiments, the probe device 100 may image through the cervix to deliver laser energy to the fetus brain.

Measurements by the probe device 100 that indicate intrapartum hypoxia aid in decisions to avoid further exposure to the fetus of such hypoxia by indicating a need for corrective actions such as cesarean section or an assisted delivery. Further, the measurements provided by the probe device 100 may also identify fetuses with normal oxygen saturation that may continue with the process of labor. Thus, use of the probe device 100 may reduce a number of fetuses that are overexposed to prolonged hypoxia and reduce a rate of unnecessary cesarean sections.

A signal may be "generated" by direct or indirect calculation or measurement, with or without the aid of a sensor.

For the purposes of describing and defining the present invention, it is noted that reference herein to a variable being a "function" of (or "based on") a parameter or another variable is not intended to denote that the variable is exclusively a function of or based on the listed parameter or variable. Rather, reference herein to a variable that is a "function" of or "based on" a listed parameter is intended to be open ended such that the variable may be a function of a single parameter or a plurality of parameters.

It is also noted that recitations herein of "at least one" component, element, etc., should not be used to create an inference that the alternative use of the articles "a" or "an" should be limited to a single component, element, etc.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A system for fetal brain assessment during delivery comprising:
   one or more processors;
   one or more memory modules communicatively coupled to the one or more processors;
   an ultrasound machine comprising a display and communicatively coupled to the one or more memory modules;
   a probe device comprising an optical fiber assembly and a transducer, the probe device communicatively coupled to the ultrasound machine; and machine readable instructions stored in the one or more memory modules that cause the system to perform at least the following when executed by the one or more processors:

transmit a plurality of (ultrasound) US signals from the transducer of the probe device and a plurality of (photoacoustic) PA signals from the optical fiber assembly of the probe device toward a fetal brain upon insertion of the probe device into a vaginal birth canal of a maternal pelvis during active labor, wherein the transmitted PA signals comprise laser pulses configured to be tunable based on a change in wavelength;

receive, into the transducer of the probe device, a plurality of reflected US and PA signals comprising a plurality of reflected US signals and a plurality of reflected PA signals, the plurality of reflected US signals comprising sound waves bounced back from the fetal brain in response to the plurality of US signals, the plurality of reflected PA signals comprising ultrasonic waves generated by the fetal brain in response to the plurality of PA signals;

transmit, via the probe device, the received plurality of reflected US and PA signals to the ultrasound machine;

generate one or more images of the fetal brain at least partially based on the received plurality of reflected US and PA signals in real-time; and display the one or more images on the display of the ultrasound machine.

2. The system of claim 1, further comprising machine readable instructions to:

generate an interleaved image of the fetal brain at least partially based on the received plurality of reflected US and PA signals in real-time; and display the interleaved image of the fetal brain comprising an image of blood vessels, the venous and arterial blood vessels respectively comprising a superior sagittal sinus and one or more portions of an anterior cerebral artery within the fetal brain.

3. The system of claim 2, further comprising machine readable instructions to:

determine a first measurement of oxygen saturation of a first section of the superior sagittal sinus from the interleaved image based on a PA signal difference between oxy-hemoglobin and deoxy-hemoglobin values at the first section;

determine a second measurement of oxygen saturation of a second section of the one or more portions of an anterior cerebral artery from the interleaved image based on a PA signal difference between oxy-hemoglobin and deoxy-hemoglobin values at the second section;

determine a differential between arterial and venous oxygen saturation of the fetal brain based on the determined first and second measurements of oxygen saturation; and determine an estimated oxygen measurement at least partially based on the determined differential and the first and second measurements of oxygen saturation, the estimated oxygen measurement as at least one of a cerebral metabolic rate of oxygen and a global brain oxygen consumption parameter.

4. The system of claim 2, further comprising machine readable instructions to:

delineate the venous and arterial blood vessels using Color Doppler US;

determine diameters at a first section of the venous blood vessel and a second section of the arterial blood vessel; and determine a respective blood flow velocity measurement through the venous and arterial blood vessels at least partially based on a velocity time integral of the respective first and second sections and the respective determined diameters.

5. The system of claim 2, further comprising machine readable instructions to:

obtain an image of a cerebral cortex of the fetal brain from the probe device utilizing a power Doppler US (PDU), the image comprising a plurality of pixels containing PDU information and respectively including a PDU intensity signal;

analyze the PDU intensity signals through a normalization procedure to obtain an estimated fractional moving blood volume (FMBV) corresponding to a set of fetal blood vessels; and determine a time-averaged blood perfusion (TABP) in the cerebral cortex based on the analyzed PDU intensity signals, wherein the TABP is representative of a percentage of blood movement in a defined area of a fetal blood vessel.

6. The system of claim 5, wherein normalization procedure comprises machine readable instructions to:

set a selected PDU intensity signal to 1 as a normalization value;

set a set of PDU intensity signals having a value greater than the selected PDU intensity signal to 1; and set a set of PDU intensity signals having a value less than the selected PDU intensity signal to a corresponding fraction of 1.

7. The system of claim 1, wherein:

the probe device comprises the optical fiber assembly communicatively coupled to a laser and an active surface communicatively coupled to the transducer.

8. The system of claim 7, wherein:

the plurality of US signals are transmitted from the active surface of the probe device as a series of sound wave signals.

9. The system of claim 7, wherein:

the plurality of PA signals are transmitted from the optical fiber assembly as a series of laser pulse signals from the laser.

10. The system of claim 1, wherein the plurality of US signals and the plurality of PA signals are transmitted from respectively the transducer and the optical fiber assembly of the probe device toward a fetal brain when the probe device is positioned within a distance range from the fetal brain.

11. The system of claim 10, wherein the distance range is less than 25 mm from a portion of a superior sagittal sinus and one or more portions of an anterior cerebral artery within the fetal brain.

12. The system of claim 11, wherein the one or more portions of the anterior cerebral artery comprises pericallosal and callosomarginal arteries of the anterior cerebral artery.

13. A method for multi-parametric, non-invasive, and real-time assessment of oxygen in the fetal brain during labor and delivery of a fetus through a vaginal birth canal of a maternal pelvis, the method comprising:

positioning a probe device in the maternal pelvis within a distance range from the fetal brain during active labor, wherein the probe device comprises an optical fiber assembly and a transducer, and the probe device is communicatively coupled to an ultrasound (US) machine and one or more processors;

transmitting a plurality of US signals from the transducer of the probe device and a plurality of photoacoustic (PA) signals from the optical fiber assembly of the probe device toward the fetal brain;

receiving, into the transducer of the probe device, a plurality of reflected US and PA signals comprising a plurality of reflected US signals and a plurality of reflected PA signals, the plurality of reflected US signals comprising sound waves bounced back from the fetal brain in response to the plurality of US signals, the plurality of reflected PA signals comprising ultrasonic waves generated by the fetal brain in response to the plurality of PA signals;

transmitting, via the probe device, the received plurality of reflected US and PA signals to the US machine;

generating one or more images of venous and arterial blood flow of respective blood vessels in the fetal brain based on the received plurality of reflected US and PA signals;

displaying in real-time the one or more images via the US machine;

measuring oxygen saturation of the respective venous and arterial blood vessels based on data from the one or more images; and estimating an oxygen measurement in the fetal brain during active labor based on the measured oxygen saturation.

14. The method of claim 13, wherein the one or more images comprise a first image of venous blood flow in a venous blood vessel comprising a superior sagittal sinus and a second image of arterial blood flow of an arterial blood vessel comprises one or more portions of an anterior cerebral artery within the fetal brain; and displaying in real-time the one or more images via the US machine comprises at least one of:

displaying an interleaved image of the first image and the second image on a display of the US machine; and displaying the first image and the second image separately on the display of the US machine.

15. The method of claim 14, wherein measuring oxygen saturation of the respective venous and arterial blood vessels based on data from the one or more images comprises:

determining a first measurement of oxygen saturation of a first section of the superior sagittal sinus from the one or more images based on a PA signal difference between oxy-hemoglobin and deoxy-hemoglobin values at the first section;

determining a second measurement of oxygen saturation of a second section of the one or more portions of an anterior cerebral artery from the one or more images based on a PA signal difference between oxy-hemoglobin and deoxy-hemoglobin values at the second section; and determining a differential between arterial and venous oxygen saturation of the fetal brain based on the determined first and second measurements of oxygen saturation.

16. The method of claim 15, wherein estimating the oxygen measurement comprising estimating at least one of a metabolic rate of oxygen and a global brain oxygen consumption parameter in the fetal brain during active labor based on the determined differential and the first and second measurements of oxygen saturation.

17. The method of claim 14, wherein the one or more portions of the anterior cerebral artery comprises pericallosal and callosomarginal arteries of the anterior cerebral artery.

18. The method of claim 13, wherein:

the probe device comprises the optical fiber assembly communicatively coupled to a laser and an active surface communicatively coupled to the transducer.

19. The method of claim 18, wherein:

the plurality of US signals are transmitted from the active surface of the probe device as a series of sound wave signals; and the plurality of PA signals are transmitted from the optical fiber assembly as a series of laser pulse signals from the laser.

20. The method of claim 13, further comprises:

determine a pose of a fetal head during active labor at least partially based on the plurality of reflected US and PA signals.

* * * * *